United States Patent [19]

Berke et al.

[11] Patent Number: 5,244,653
[45] Date of Patent: Sep. 14, 1993

[54] GLYCINE ANHYDRIDE DIMETHYLOL AS A BIOCIDE AND PRESERVATIVE

[75] Inventors: Philip A. Berke, Madison; William E. Rosen, Summit, both of N.J.

[73] Assignee: ISP Chemicals Inc., Chatham, N.J.

[21] Appl. No.: 694,252

[22] Filed: May 1, 1991

[51] Int. Cl.$^5$ .................... A01N 43/48; A61K 7/06; A61K 31/495

[52] U.S. Cl. .................... 424/70; 162/162; 252/405; 514/401; 514/247; 514/255; 514/337; 514/355; 426/521; 544/385

[58] Field of Search .............. 514/337, 255; 544/355; 424/70; 422/423; 426/521

[56] References Cited

U.S. PATENT DOCUMENTS 3,136,598 6/1964 Kokorudz .................... 21/58
3,350,317 10/1967 Symes .................... 252/99

*Primary Examiner*—Dale R. Ore
*Attorney, Agent, or Firm*—Bacon & Thomas

[57] ABSTRACT

The use of glycine anhydride dimethylol, also known as 1,4-bis(hydroxymethyl)-2,5-piperazinedione, comprising the formula

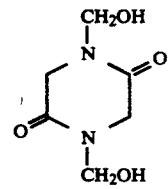

to kill microorganisms present in or on a host substance and to preserve products susceptible to contamination by a variety of microorganisms is disclosed.

11 Claims, No Drawings

GLYCINE ANHYDRIDE DIMETHYLOL AS A BIOCIDE AND PRESERVATIVE

BACKGROUND OF THE INVENTION

1. Technical Field of the Invention

This invention relates to the use of glycine anhydride dimethylol, as a biocide and an antimicrobial agent to kill microorganisms present in or on substances and to preserve a variety of substances susceptible to microbial contamination.

2. Description of the Prior Art

Glycine anhydride dimethylol, also known as 1,4-bis(hydroxymethyl)-2,5-piperazinedione is a known chemical compound prepared by reacting glycine anhydride, also referred to as 2,5-piperazinedione with formaldehyde according to the following formula:

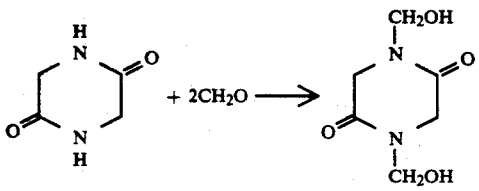

See, e.g. Cherbuliez et al., Helv. Chim. Octa, 5, 678, 688 (1923).

SUMMARY OF THE INVENTION

It is an object of the invention to provide a method for killing microorganisms present in or on a host substance by administering to the host an effective biocidal amount of glycine dimethylol anhydride.

It is a further object of the invention to provide a method for preserving products susceptible to contamination by microorganisms by incorporating into the product an antimicrobial effective amount of glycine anhydride dimethylol.

It is a further object of the invention to provide preserved products, that is products which have been protected against contamination by microorganisms, containing glycine anhydride dimethylol in an amount which is effective to preserve the product against contamination by microorganisms.

Other objects and advantages of the invention will be evident to those of skill in the art upon review of the detailed description which follows.

DETAILED DESCRIPTION OF THE PREFERRED EMBODIMENTS

This invention is based upon the discovery that glycine anhydride dimethylol, also known as 1,4-bis(hydroxymethyl)-2,5-piperazinedione, represented by the formula:

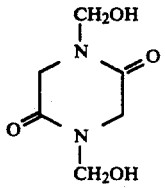

exhibits biocidal activity against a wide range of microorganisms, including bacteria, yeast and mold. This compound, therefore, is an effective biocidal agent which kills microorganisms present in or on a host substance and inhibits microbial growth in or on a variety of substances and products, whether they be solid, liquid or emulsion form. Such products include, but are not limited to, cosmetics, foodstuffs, pharmaceuticals, paints, cutting oils or fluids, agricultural products, oil drilling fluids, lubricants, paper industry products, embalming solutions, cold sterilized medical and dental equipment, cooling towers, fabric impregnation, latexes, swimming pools, inks, household disinfectants, waxes and polishes, toilet bowl cleaners, bathroom cleaners, laundry detergents, soaps, wood preservatives, hospital and medical antiseptic and adhesives. Of these products, foodstuffs, pharmaceuticals, cosmetic and personal hygiene products such as shampoos are of particular interest.

Other uses of glycine anhydride dimethylol according to the invention include industrial uses where the compound is used to control microbial growth, such as for slime control in the effluent of paper mills.

By virtue of its biocidal activity, glycine anhydride dimethylol can be used to kill microorganisms which have contaminated a host substance or as a preservative to inhibit and prevent growth of microorganisms in substances susceptible to microbial growth. The compound is also effective in disinfecting and/or sterilizing surfaces prone to contamination by microorganisms. The effective amount of glycine anhydride dimethylol required will, of course, vary depending upon the mode of use, e.g., as a biocidal agent to kill an established colony of microorganism or as a preservative to inhibit growth of microorganisms, to which it is directed. Those of skill in the art will have no difficulty in determining the requisite effective amounts for particular uses.

When treating a host substance, the glycine anhydride dimethylol can be administered thereto as a solid powder, in aqueous solution or in an emulsion alone or with other ingredients, including other biocides and/or medicaments. The amount of glycine anhydride dimethylol required to be incorporated into a product for preservation will also vary depending upon the product being protected and the environment of use. Generally, products containing less than about 1.0% by weight of glycine anhydride dimethylol will be effectively protected from microbial contamination in most environments. Principally for economic reasons, concentrations less than about 0.5% by weight are preferred. Those of skill in the art will have little difficulty in selecting specific amounts required for particular uses based upon the information contained herein, especially in the examples.

In addition to glycine anhydride dimethylol, other conventional ingredients may be incorporated into the product requiring preservation, including other antimicrobial agents, suspending agents, wetting agents, antiscaling agents, corrosion inhibitors and pH control agents. The selection of the particular addition ingredients, if any, will depend upon the particular product requiring preservation.

When blending with the product to be preserved, the glycine anhydride dimethylol may be incorporated as a solid powder or in aqueous solution. The powder is the preferred form since it is easier to handle than a liquid. When the application calls for a liquid formulation, the powder can be readily dissolved in aqueous media. The glycine anhydride dimethylol may be blended into the product as the sole antimicrobial agent or as part of an antimicrobial system with other antimicrobial agents. Such systems are particularly effective when it is necessary to preserve a product against a wide range of microorganisms. By careful selection of the antimicrobial agents in the system, antimicrobial activity against a particular group of microorganisms can be optimized for a particular product. When using an antimicrobial system it is further advantageous to incorporate the antimicrobial agents in a common solvent, such as propylene glycol, which also exhibits antimicrobial activity and so serves the dual function of solvent and antimicrobial agent.

This invention thus provides an effective means for preserving substances susceptible to microbial contamination by inhibiting growth of bacterial, yeast and mold. The compound of the invention is readily incorporated into a variety of forms including liquids, solids and emulsions.

To further illustrate the various aspects of the invention, the following examples are provided. However, it is to be understood that their purpose is entirely illustrative and in no way intended to limit the scope of the invention. In the examples, all percentages are given by weight unless otherwise noted.

EXAMPLE I

Preparation of glycine anhydride dimethylol

To a stirred slurry of 11.4 g. (0.1 mole) of glycine anhydride in 41.0 ml. of water was added 16.2 g. (0.2 mole) of 37% aqueous formaldehyde. Addition of 0.10 g. of 10% aqueous sodium hydroxide solution caused the suspended solids to dissolve, followed by formation of a heavy white precipitate. The mixture was heated to 70° C., by which time all solids dissolved. On cooling to room temperature, white crystals separated. The crystals were collected, washed with cold water, and dried in vacuum at 100° C. for 1 hour. The white crystalline product, glycine anhydride dimethylol weighed 12.6 g. (72.4% yield), m.p. 185°–188° C. dec. Anal. Calcd. for $C_6H_{10}N_2O_4$ (174.16): N, 16.09. Anal. Found: N, 1617.

EXAMPLE 2

Microbiological Activity

A. Minimum Inhibitory Concentration (MIC)

Aqueous solutions of 1% glycine anhydride dimethylol were serially diluted with sterile distilled water, and aliquots of different concentrations were mixed with equal volumes of inoculated culture medium. AOAC broth was used for the bacterial culture media, and Sabourand Liquid Medium was used for the yeast and mold cultures. The mixtures of glycine anhydride dimethylol solution and culture media were incubated at 35° C. for 48 hours for bacteria and yeast, and at 26° C. for 7 days for mold. Microbial growth or no growth were determined by visual inspection for cloudiness. The MIC for a given microorganism was the lowest concentration of antimicrobial that remained clear after the incubation period. Results are as follows:

| Bacteria | | | MIC |
|---|---|---|---|
| Gram-Neg. | Pseudomonas aeruginosa | ATCC 9027 | 310 ppm |
| Gram-Pos. | Staphylococcus aureus | ATCC 6538 | 310 ppm |
| Yeast | Candida albicans | ATCC 10231 | 310 ppm |
| Mold | Aspergillus niger | ATCC 16404 | 2500 ppm |

B. Challenge tests on a cosmetic emulsion

A typical cosmetic emulsion was prepared for microbiological challenge testing. The emulsion was prepared in four different variations: with no preservative added, with 0.05% glycine anhydride dimethylol, with 0.10% glycine anhydride dimethylol, and with 0.20% glycine anhydride dimethylol. The formulation used for challenge testing was as follows:

| | % W/W | | | |
|---|---|---|---|---|
| Phase A | | | | |
| Water, Demineralized | 67.90 | 67.85 | 67.80 | 67.70 |
| Triethanolamine, 99% | 1.00 | 1.00 | 1.00 | 1.00 |
| Phase B | | | | |
| Laneth-5 (and) Ceteth-5 (and) Oleth-5 (and) Steareth-5 | 0.50 | 0.50 | 0.50 | 0.50 |
| Mineral Oil | 2.50 | 2.50 | 2.50 | 2.50 |
| Stearic Acid, XXX | 5.00 | 5.00 | 5.00 | 5.00 |
| Cetyl Alcohol | 1.00 | 1.00 | 1.00 | 1.00 |
| Glyceryl Stearate (and) PEG-100 Stearate | 1.50 | 1.50 | 1.50 | 1.50 |
| Phase C | | | | |
| Citric Acid (30% Solution) | 0.60 | 0.60 | 0.60 | 0.60 |
| Phase D | | | | |
| Water, Demineralized | 20.00 | 20.00 | 20.00 | 20.00 |
| Glycine Anhydride Dimethylol (GAD) | — | 0.05 | 0.10 | 0.20 |
| | 100.00 | 100.00 | 100.00 | 100.00 |

Challenge tests were carried out using four different microorganisms, and microbial counts were made after incubating 24, 48, and 72 hours. The USP Antimicrobial Preservative Effectiveness Test NUPS XXII Method) was used with minor modifications.

| | No Preservative | 0.05% GAD | 0.10% GAD | 0.20% GAD |
|---|---|---|---|---|
| MICROBIAL COUNTS, 24 HOURS | | | | |
| P. aeruginosa | $9 \times 10^5$ | <10 | 50 | 100 |
| S. aureus | $2 \times 10^6$ | $4 \times 10^4$ | $5 \times 10^4$ | $2 \times 10^3$ |
| C. albicans | $2.5 \times 10^4$ | $1 \times 10^4$ | 50 | <10 |
| A. niger | $5 \times 10^4$ | 500 | <10 | <10 |
| MICROBIAL COUNTS, 48 HOURS | | | | |
| P. aeruginosa | $1 \times 10^6$ | <10 | 15 | 60 |
| S. aureus | $6 \times 10^6$ | 100 | 15 | 200 |
| C. albicans | $2 \times 10^4$ | $1 \times 10^4$ | <10 | <10 |
| A. niger | $4 \times 10^4$ | <10 | <10 | <10 |
| MICROBIAL COUNTS, 72 HOURS | | | | |
| P. aeruginosa | $1 \times 10^6$ | <10 | <10 | <10 |
| S. aureus | $5 \times 10^6$ | <10 | <10 | <10 |
| C. albicans | $2 \times 10^4$ | $1 \times 10^3$ | <10 | <10 |
| A. niger | $3 \times 10^4$ | <10 | <10 | <10 |

C. Challenge tests on a shampoo

A typical shampoo was prepared both with and without glycine anhydride dimethylol, and then challenge tested with several microorganisms. The USP Antimicrobial Preservative Effectiveness Test. (USPXXII Method) was used with minor modifications, with microbial counts made after 24, 48 and 72 hours. The same microorganisms (same ATCC numbers) were used as noted above.

The shampoo formulations were as follows:

| | % W/W | |
|---|---|---|
| Phase A | | |
| Water, Demineralized | | |
| Ammonium Lauryl Sulfate | 25.00 | 25.00 |
| Cocamide DEA | 6.50 | 6.50 |

| | % W/W | |
|---|---|---|
| Cocamideopropyl Botaine | 5.00 | 5.00 |
| Phase B | | |
| Citric Acid, 30% Solution | * | * |
| Phase C | | |
| Water, Deionized | 20.00 | 20.00 |
| Glycine Anhydride Dimethylol | — | 0.20 |
| | 100.00 | 100.00 |

*qs to pH 6

Microbial challenge test results were as follows:

| | No Preservative | 0.2% GAD |
|---|---|---|
| MICROBIAL COUNTS, 24 HOURS | | |
| P. aeruginosa | 5 × 10$^5$ | 50 |
| S. aureus | <10 | <10 |
| C. albicans | 2 × 10$^4$ | <10 |
| A. niger | 5 × 10$^4$ | <10 |
| MICROBIAL COUNTS, 48 HOURS | | |
| P. aeruginosa | 1 × 10$^4$ | <10 |
| S. aureus | <10 | <10 |
| C. albicans | 2 × 10$^4$ | <10 |
| A. niger | 1 × 10$^5$ | <10 |
| MICROBIAL COUNTS, 72 HOURS | | |
| P. aeruginosa | 50 | <10 |
| S. aureus | <10 | <10 |
| C. albicans | 2 × 10$^4$ | <10 |
| A. niger | 5 × 10$^3$ | <10 |

D. Preservation of milk

The microbial spoilage of whole milk at room temperature was prevented by the incorporation of 0.16% glycine anhydride dimethylol. The following series of tests were terminated after 59 days.

| Preservative Added to Whole Milk | Time to Spoilage (i.e. development of odor, curdling, etc.) |
|---|---|
| none | 10 days |
| 0.16% | 59+ days |
| 0.16% | 59+ days |
| 0.32% | 59+ days |
| 0.32% | 59+ days |

While the invention has been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

What is claimed is:

1. A method for protecting a substance susceptible to contamination by bacteria, yeast and mold against contamination by said microorganisms comprising incorporating in the substance an effective microbial growth inhibiting amount of glycine anhydride dimethylol of the formula:

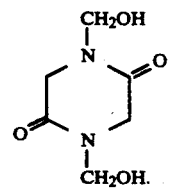

2. The method as defined by claim 1, wherein said glycine anhydride dimethylol is incorporated into said substance in an amount less than about 1.0% by weight.

3. The method as defined by claim 1, wherein said glycine anhydride dimethylol is incorporated into said substance in an amount less than about 0.5% by weight.

4. The method as defined by claim 1, wherein said glycine anhydride dimethylol is incorporated into said substance in solid form.

5. The method as defined by claim 1, wherein said glycine anhydride dimethylol is incorporated into said substance in aqueous solution.

6. The method as defined in claim 1, wherein said substance is a cosmetic product.

7. The method as defined in claim 1, wherein said substance is a personal hygiene product.

8. The method as defined in claim 7, wherein said personal hygiene product is a shampoo.

9. The method as defined in claim 1, wherein said substance is a pharmaceutical product.

10. The method as defined in claim 1, wherein said substance is a foodstuff.

11. The method as defined in claim 1, wherein said substance is the effluent from a paper mill.

* * * * *